United States Patent [19]

Kolombos

[11] 4,112,011

[45] Sep. 5, 1978

[54] OLIGOMERIZATION PROCESS

[75] Inventor: Alexander John Kolombos, Thames Ditton, England

[73] Assignee: The British Petroleum Company Limited, London, England

[21] Appl. No.: 804,628

[22] Filed: Jun. 8, 1977

[30] Foreign Application Priority Data

Jun. 22, 1976 [GB] United Kingdom ............... 25884/76

[51] Int. Cl.$^2$ ............................................... C07C 3/20
[52] U.S. Cl. ........................................... 260/683.15 R
[58] Field of Search ................................ 260/683.15 R

[56] References Cited

U.S. PATENT DOCUMENTS

| | | | |
|---|---|---|---|
| 3,228,917 | 1/1966 | Childers | 260/683.15 R |
| 3,370,101 | 2/1968 | Hayes et al. | 260/683.15 R |
| 3,773,853 | 11/1973 | Brennan et al. | 260/683.15 R |

*Primary Examiner*—C. Davis
*Attorney, Agent, or Firm*—Brooks, Haidt, Haffner & Delahunty

[57] ABSTRACT

A process for producing unsaturated hydrocarbons by oligomerizing a $C_3$–$C_8$ monoolefin in the presence of a gallium catalyst deposited on a support.

7 Claims, No Drawings

OLIGOMERIZATION PROCESS

The present invention relates to a process for the oligomerisation of olefins.

Accordingly, the present invention is a process for producing unsaturated hydrocarbons comprising subjecting a $C_3$-$C_8$ mono-olefinic hydrocarbon to oligomerisation in the presence of a catalyst comprising a compound of gallium deposited on a support.

The $C_3$-$C_8$ mono-olefinic hydrocarbon feedstock of the present invention includes straight or branched chain isomers and mixtures of one or more such isomers. Olefins selected from propylene, butene, isobutene, pentene and isopentene are preferable.

Preferred examples of gallium compounds are gallium oxide and gallium ions exchanged with the surface hydroxyls of a surface active oxide such as hydrated silica, hydrated alumina or hydrated silica-alumina.

The amount of gallium present in such catalyst compositions may vary between 0.01 and 20%, preferably between 0.1 and 6% by weight of the total support in the catalyst composition.

Suitable examples of support for the gallium catalysts are aluminas such as eta-alumina, gamma alumina and boehmite; aluminas, silicas and silica-aluminas with surface hydroxyl groups which may be exchanged by ions of metals selected from gallium and aluminium which may in turn be ion-exchanged with metal ions such as those of iron, cobalt and nickel; and refractory gallium oxide. Silica supports, especially those with exchanged surface hydroxyl groups are, however, preferred.

The catalyst composition of the present invention may also contain other metals such as palladium, platinum, indium, germanium, thallium, chromium, tin, zinc, iron, cobalt and/or nickel in small quantities to improve the activity thereof.

The catalyst may be prepared by impregnating the support with an aqueous solution of a soluble gallium compound, e.g. gallium nitrate. The paste so formed is evaporated to dryness under vacuum and then pyrolysed at elevated temperature in a stream of air. When surface active silica, alumina, or silica-alumina are used as support, the hydroxyl groups are preferably exchanged by gallium ions.

The catalyst so prepared may be formed as a fixed bed and may be activated in the reactor tube itself. The activation may be carried out by purging the catalyst with a suitable gas such as nitrogen or air at a temperature of between 400° and 650° C.

The mono-olefinic hydrocarbon feedstock is thereafter passed over the catalyst at a temperature between 20° and 500° C. preferably between 50° and 250° C. The reaction may be carried out in the presence of a diluent which is inert under the reaction conditions such as nitrogen.

The oligomerisation reaction is suitably carried out under reaction pressures ranging from atmospheric to 1500 psig, preferably from 50 to 1500 psig. The reaction pressures to be used within the specified range would depend upon the nature of the feedstock being oligomerised. That is, lower feedstock within the $C_3$-$C_8$ range require relatively higher pressures in comparison with a higher feedstock within the same range. The products of the reaction are then isolated.

Oligomeric products produced by the process of the present invention are useful as feedstocks for various reactions. For example, $C_8$ hydrocarbons, produced by oligomerising $C_4$ olefins such as isobutene, may be used for producing phthalate esters which find wide use as plasticizers.

The oligomerised products may be cyclised to an aromatic hydrocarbon directly without isolation over the same catalyst. For example the oligomers of propylene may be converted to benzene and the oligomer of isobutene may be cyclised to xylenes.

The invention is further illustrated with reference to the accompanying examples.

Preparation of 6% $Ga_2O_3$/Eta-alumina catalyst

To a solution of 10 g gallium nitrate ($Ga(NO_3)_3.8H_2O$) in approximately 30 ml of distilled water, 26.6 g eta-alumina was added and stirred into a paste. The paste was evaporated to dryness in a vacuum oven overnight and heated in air at 550° C. for 6 hours to give gallium oxide (6% wt. gallium) on eta-alumina.

Preparation of gallium exchanged silica catalyst 400 g of Crossfields U 40 silica gel was hydrolysed by standing under 1l distilled water for 3 days. The silica gel was decanted dry and stood under 4l of 2N nitric acid for 6 hours, and then finally washed with 12l of distilled water in a Buchner funnel. The silica gel was dried at 200° C. for 72 hours and calcined at 550° C. in air for 72 hours.

4.5 g of gallium nitrate, $Ga(NO_3)_3.9H_2O$, was dissolved in 200 ml of distilled water. 30 ml of the prepared silica gel was packed into a glass column and the gallium nitrate solution was percolated through the column for 18 hours. The catalyst was finally washed with 1500 ml of distilled water and dried in a vacuum overnight. The gallium exchanged silica catalyst (0.6% wt. gallium) was heated in air at 550° C. for 6 hours before use.

Similar catalysts containing higher percentage of gallium (e.g. 1.8% wt.) were prepared by exchanging further quantities of gallium nitrate under controlled pH conditions.

Preparation of $Ga_2O_3$/silica catalyst 4.9 g gallium nitrate, $Ga(NO_3)_3.8H_2O$ dissolved in 15 ml distilled water was added to 13 g Crossfields U 40 silica suspended in 15 ml distilled water. The mixture was evaporated to dryness in a vacuum overnight and heated in air at 550° C. for six hours to give gallium oxide (6% wt. Ga) on silica.

EXAMPLE 1

A polyisobutene plant raffinate stream approximately containing butene-1 (9%), butene-2 (60%), isobutene (10%) and butane (21%) was passed over gallium (0.6% wt.) exchanged silica catalyst at a reaction pressure of 800 psig, a temperature of 125° C. and LHSV3. After 20 hours on stream, of the feed converted, 79.4% was a mixture of open chain $C_8$ isomers and 18% was a mixture of $C_{12}$ isomers.

EXAMPLE 2

Isobutene was passed over a gallium (1.8% wt Ga) exchanged silica catalyst at atmospheric pressure, a temperature of 200° C. and a contact time of 10.5 seconds. 67.8% of the isobutene fed was converted to give 43.8% wt of open chain $C_8$ isomers and 14.4% wt of open chain $C_{12}$ isomers.

EXAMPLE 3

Using the same catalyst as Example 2 above but using 3-methyl-butene-1 as feed and a contact time of 11.7 seconds, 6.2% wt (59.6% selectivity) of open chain $C_{10}$ isomers were formed.

EXAMPLE 4

The above example was repeated using 2-methylbutene-2 as feed. Under the same conditions, 5.6% wt (52% selectivity) of open chain $C_{10}$ isomers were formed.

EXAMPLE 5

Propylene was passed over a gallium (1.8% wt Ga) exchanged silica catalyst at atmospheric pressure, a temperature of 200° C. and a contact time of 10.5 seconds. The major product was found to be branched chain pentenes.

EXAMPLE 6

When isobutene was passed over a gallium oxide (6% wt gallium)/eta-alumina catalyst at a reaction temperature of 550° C. and a residence time of 5.5 sec., after 1.5 minutes on stream 96.3% of the isobutene was converted. The major products (expressed as percent weight yield) were butenes (7.5%), butanes (15.0%), $C_1$–$C_3$ hydrocarbons (26.6%) and aromatics (47.0%). Xylenes made up 25.7% weight yield of the aromatics. With total $C_4$s recycle the selectivity to aromatics is 60.6% and to xylenes 33.2%.

I claim:

1. A process for producing unsaturated hydrocarbons which comprises subjecting a $C_3$ to $C_8$ mono-olefinic hydrocarbon to a temperature of from about 20° to 500° C. at a pressure of from about 50 to 1500 psig in the presence of a catalyst prepared by admixing a water-soluble gallium compound with an aluminia, silica, or silica-aluminia containing surface hydroxyl groups so that at least part of the surface hydroxyl groups have been exchanged with gallium ions.

2. A process as defined in claim 1 wherein said catalyst has been activated by purging the catalyst with nitrogen or air at a temperature of between about 400° and 650° C.

3. A process as defined in claim 1 wherein said soluble gallium compound is gallium nitrate.

4. A process as defined in claim 1 wherein said catalyst contains at least one of the metals palladium, platinum, indium, germanium, thallium, chromium, tin, zinc, iron, cobalt and nickel.

5. A process as defined in claim 1 wherein the water-soluble gallium compound is admixed with a silica containing surface hydroxyl groups.

6. A process according to claim 1 wherein the gallium is exchanged with a metal ion selected from iron, cobalt and nickel.

7. A process according to claim 1 wherein the oligomerisation is carried out in the presence of nitrogen as an inert diluent.

* * * * *